United States Patent [19]
Farr

[11] 3,953,609
[45] Apr. 27, 1976

[54] METHOD FOR THE GROWTH RESTRICTION OF UNDESIRABLE DIGESTIVE SYSTEM BACTERIA IN ANIMALS AND THE ESTABLISHMENT OF LACTOBACILLUS LACTIS NRRL B-5628

[75] Inventor: Stewart M. Farr, Sarasota, Fla.

[73] Assignee: Microlife Technics, Inc., Sarasota, Fla.

[22] Filed: Feb. 6, 1974

[21] Appl. No.: 440,250

[52] U.S. Cl. .................... 426/2; 426/71; 426/807; 424/93
[51] Int. Cl.² .................................. A23K 1/00
[58] Field of Search ............ 426/4, 71, 807; 424/93; 195/96, 100, 102

[56] References Cited
UNITED STATES PATENTS

| | | | |
|---|---|---|---|
| 3,326,693 | 6/1967 | Reuter | 426/43 |
| 3,561,977 | 2/1971 | Rothchild et al. | 99/109 |
| 3,677,897 | 7/1972 | Jeffreys | 195/96 |

FOREIGN PATENTS OR APPLICATIONS

| | | | |
|---|---|---|---|
| 2,427M | 3/1964 | France | 424/93 |
| 46-15643 | 4/1971 | Japan | 424/93 |

*Primary Examiner*—Norman Yudkoff
*Assistant Examiner*—Curtis P. Ribando
*Attorney, Agent, or Firm*—Miller, Morriss, Pappas & McLeod

[57] ABSTRACT

The method of orally feeding animals including humans *Lactobacillus lactis* NRRL B-5628 to restrict the growth of other digestive system (such as mouth, crop and/or stomach) bacteria is described. NRRL B-5628 is particularly useful in the treatment of scouring, diarrhea or colibacillosis in baby pigs and other newborn animals by reducing the intestinal population of *E. coli* as the native coliform bacterium. The oral feeding of NRRL B-5628 is also used in farrowing sows to reduce intestinal bacteria and in turn to reduce such bacterial populations in the newborn pigs. Mastitis-metrites syndrome in gilts, sows and cows is reduced by such oral feeding.

8 Claims, No Drawings

METHOD FOR THE GROWTH RESTRICTION OF UNDESIRABLE DIGESTIVE SYSTEM BACTERIA IN ANIMALS AND THE ESTABLISHMENT OF LACTOBACILLUS LACTIS NRRL B-5628

SUMMARY OF THE INVENTION

The present invention relates to a method for restricting the growth of undesirable digestive system bacteria and establishment of a desirable mucosal flora by the oral feeding of *Lactobacillus lactis* NRRL B-5628. In particular, the present invention relates to the treatment of scouring in baby pigs and other newborn animals, including chickens and humans.

PRIOR ART

Native or ingested intestinal bacteria under certain weakened or diseased intestinal conditions of an animal can cause infections and even death. Such bacteria can also cause severe weight restrictions in young growing animals by promoting loss of fluid and by preventing the complete digestion of food. Lactobacillus bacteria are known to be important to the health of chickens as disclosed in Fuller, R (*J. Appl. Bact.* 36: 131 to 139, 1973) and by Fuller, R. in *New Scientist* pages 506 to 507, Nov. 30, 1973. These bacteria particularly line the crop of the chicken or other fowl.

Animal disorders caused by such bacteria have been treated with antibiotics. Thus furazolidone suspensions have been administered to baby pigs or the mother before the farrowing of a gilt or sow. Such treatments eliminate the natural microflora of the intestine and after the treatment is eliminated, the animals are prone to more severe bacterial infection. The possibility of antibiotic contamination of the animal meat used for human consumption also exists; this in turn may encourage emergence of drug resistant bacteria which can also cause different types of infection among livestock workers and food handlers. These infections frequently do not respond to antbiotic therapy because they are caused by the resistant bacteria.

*Lactobacillus acidophilus* or other bacteria in milk or in lyophilized form has been administered to animals to reduce the problems caused by the natural intestinal bacterial population which, especially under stress condition, overgrow other bacteria. Such administered bacteria have low viability and/or are fed in low concentration and as soon as the treatment is stopped, the problems recur in the animals. Administration of the bacteria to the animals has been regarded as time consuming. This prior art is shown in Kohler et al. JAVMA 144 (11); 1294–1297 (1964); in British Patent No. 1,134,206 and in U.S. Pat. Nos. 3,326,093 and 3,480,443.

Colibacillosis or scouring (diarrhea) in baby pigs caused by *E. coli* is a major cause of economic loss in the swine industry. It is generally agreed that *E. coli* (coliform bacterium) is the chief cause of piglet death and impairment of herd performance. *E. coli* is also implicated as a causative agent of mastitis-metrites syndrome in gilts and sows.

It is therefore an object of the present invention to provide an novel bacterial concentrate which upon oral feeding rapidly reduces and replaces the natural or ingested population of bacteria in the digestive system in animals, thereby preventing recurring disorders particularly disorders in the intestine.

It is further an object of the present invention to provide such bacterial concentrates which remain effective in the digestive system for substantial periods of time even after oral feeding is discontinued.

It is particularly an object of this invention to provide prophylaxis for and therapy of colibacillosis in swine, cattle and poultry by daily feeding of bacterial concentrates.

Further object is to provide prophylaxis for and therapy of mastitis-metrites syndrome in gilts, sows and cows by daily feeding of bacterial concentrates.

These and other objects will become increasingly apparent by reference to the following description.

GENERAL DESCRIPTION

The present invention relates to the method for restricting the growth of digestive system bacteria (mouth, crop, stomach, intestine, and the like) in animals including humans which comprises orally feeding a live bacterial composition of *Lactobacillus lactis* NRRL B-5628 mixed with a growth medium to said animals in an amount sufficient to substantially reduce the number of such other digestive system bacteria. The present invention also relates to a bacterial composition useful for restricting the growth of other intestinal bacteria when fed orally which comprises live *Lactobacillus lactis* NRRL B-5628 mixed with a growth medium and a freezing stabilizing agent and which is cooled such that at least about 50 percent of the bacteria in the concentrate are viable for about 24 hours.

In animals, particularly domesticated mammals, there exists three critical periods when they are susceptible to scouring. They are (1) birth, (2) weaning and (3) just after weaning when the animal is placed on feed diet. The baby pig is an example of an animal that has severe problems with scouring. Of the three stages the most critical is when the baby pig is placed on a feed diet (2 to 3 weeks after birth), since changing the diet causes stress and at this time an effective immune antibody system is not yet fully developed in piglets. Daily feeding of compositions of *L. lactis* NRRL B-5628 to weaning baby pigs prevents or reduces the severity of scouring when the pigs are placed on feed diet.

Preferably the animals are fed at least about $10^{11}$ cells per day per kilogram of body weight. Large amounts up to $10^{15}$ cells per day per kilogram body weight can be fed to the animal without any ill effect; however, this would be expensive. Also preferably the compositions are in the form of frozen concentrates containing at least about $1 \times 10^9$ cells per milliliter and preferably about $5.0 \times 10^{10}$ up to $\times 10^{11}$ cells per milliliter which are thawed and then metered into the animals' feed supply to produce the required dosage based upon the animal's feed rate. Pastes can also be prepared containing up to $1 \times 10^{15}$ cells per gram although this is not necessary.

The growth and use of *Lactobacillus lactis* NRRL B-5628 are described in detail. Set forth in Table I are the characteristics of *Lactobacillus lactis* strain NRRL B-5628. The culture is deposited at Peoria, Ill. Northern Region U.S. Department of Agriculture laboratory and is freely available to public.

TABLE I

| Characterization of Lactobacillus lactis NRRL B-5628 | |
|---|---|
| Observation | Result |
| Optimum growth conditions | Anaerobic environment |

TABLE I-continued

Characterization of Lactobacillus lactis NRRL B-5628

| Observation | Result |
| --- | --- |
| Growth with: | at 37°C[a] |
| 2% NaCl | 3 × 10² cfu/ml |
|  | control: 8 × 10⁴ cfu/ml |
| 2% sodium taurocholate | no growth |
| 2% sodium desoxycholate | growth |
| Catalase | absent |
| Pseudocatalase | absent |
| Type lactis acid produce | DL |
| Fermentation[b]: |  |
| Bromcresol purple | — |
| Glycerol | — |
| Erythritol | — |
| d(−)arabinose | — |
| l (+) arabinose | — |
| Ribose | —[c] |
| d (+) xylose | — |
| l (−) xylose | — |
| Adonitol | — |
| Methyl-xyloside | + |
| Galactose | — |
| d (+) glucose | + |
| d (−) levulose fructose | + |
| d (+) mannose | + |
| l (−) sorbose | — |
| Rhamnose | + |
| Dulcitol | — |
| Meso-inositol | — |
| Mannitol | — |
| Sorbitol | — |
| Methyl-d-mannoside | + |
| Methyl-d-glucoside | — |
| N acetyl-glucosamine | + |
| Amygdalin | — |
| Arbutine iron citrate | — |
| Aesculine iron citrate | + |
| Salicin | — |
| d (+) cellobiose | — |
| Maltose | + |
| Lactose | + |
| d (+) melibiose | — |
| Saccharose (sucrose) | + |
| d (+) trehalose | + |
| Inuline | — |
| d (+) melezitose | — |
| d (+) raffinose | + |
| Dextine | — |
| Amylose | — |
| Starch | — |
| Glycogen | — |
| Arginin[c] | —[c] |
| Glucose | +, no gas[c] |
| Teepol 0.4% | + |
| Teepol 0.6% | — |
| NaCl 4% | + |
| NaCl 6% | + |
| ONPG | +− |
| Potassium nitrate + glucose | — |
| Pyruvic acid (V.P.) | + |
| Average moles percent guanine plus cytosine | 48.0 |
| Percent homology of DNA with L. lactis 12315 | 87.0 |

[a]95% nitrogen, 5% CO₂ atmosphere in evacuated metal cylinder
[b]API test pack system
[c]These characteristics, when negative, are typical of Thermobacteria.

The organism is not *Lactobacillus acidophilus* based upon the above characteristics since this organism has an average moles percent of guanine plus cytosine in the DNA of 35.5. NRRL B-5628 was isolated from the intestinal byproducts of the inventor who has ingested large amounts of various Lactobacillus bacteria experimentally for many years. NRRL B-5628 is non toxic to lower animals and humans even in large amounts. The deposit at NRRL is characterized as *Lactobacillus acidophilus* Farr strain; however, the name is inaccurate. Intestinal *Lactobacillus acidophilus* has very different characteristics as can be seen from U.S. Pat. No. 3,326,693.

NRRL B-5628 is gram positive, non-motile rod, occurring singly, in pairs and in short claims. The dimensions are variable. Gelatin is liquefied. Acid coagulation occurs in nonfat milk. NRRL B-5628 is resistant to the amounts of antibiotics shown in Table II.

TABLE II

Chloromycetin (10 mcg.)
Erythromycin (5 mcg.)
Kanamycin (10 mcg.)
Neomycin (10 mcg.)
Novobiocin (10 mcg.)
Penicillin (5 units)
Streptomycin (5 mcg.) and
Tetracycline (10 mcg.)

*Lactobacillus lactis* NRRL B-5628 exhibits an average guanine plus cytosine content of 48% and a thermal melting value of 88.5°C by the procedure set forth in Sriranganathan, N. et al. *Applied Microbiology*, Vol. 25, pages 461 to 470 (1973). By comparison the G.C. content of *L. acidophilus* strain 4356 is 35.5% while *Lactobacillus lactis* GA has a G.C. content of 49%. The antigenic makeup of NRRL B-5628 was also studied in comparison to other lactobacillii using disc-gel immuno-diffusion assays with antiserum prepared in rabbits. The results showed five identical bands shared by *L. lactis* 39A and the NRRL B-5628 strain, indicating the bacteria are the same.

Useful media can be prepared as shown in U.S. Pat. Nos. 3,343,962 and 3,497,359.

A suggested growth medium for NRRL B-5628 is as follows:

Water — 100 gallons
Dry Sweet Whey — 34 pounds
Hydrolyzed yeast — 13 pounds
Lactose — 8 pounds
Calcium Carbonate — 8 pounds This mixture is brought to a temperature of 205°F (96.1°C) and held at this temperature for one-half hour. The medium is then cooled to 98°F(36.7°C) and inoculated at rate of (1) volume percent with a culture of *Lactobacillus lactis* NRRL B-5628 which had been propagated in milk or any conventional growth medium. The culture is incubated at 98°F (36.7°C), until the calcium carbonate is exhausted, as is indicated by discontinuance of carbon dioxide formation. This takes about 12 to 14 hours. At this point the culture is neutralized to approximately pH 6.0–6.4 and cooled to 65°F(18.3°C).

The *Lactobacillus lactis* NRRL B-5628 can be grown directly at an animal farm and fed to the animals without concentrating. This means that the animals would have to consume more liquid volume in order to obtain the required number of bacterial cells.

The bacterial cells can be separated from all or part of the liquid portion of the spent medium and concentrated by means of centrifugation. Portions of the growth medium are included with *Lactobacillus lactis* when they are concentrated so that they will remain viable. Hydrolyzed yeast is particularly useful in maintaining the bacteria before they are used. Usually centrifuging is allowed to remove only part of the liquid medium and if so, only glycerol or other stabilizing agent needs to be added if the concentrate is to be frozen. If the bacteria are centrifuged to a paste, then fresh growth medium is mixed with the cells as well. Usually the solids volume of the final concentrate is between about 10 and 20 percent, about half of which is cells and the liquid medium is between about 70 and 80 percent. If the concentrate is to be used directly, it need not be frozen and a stabilizing agent is not needed. If the concentrate is to be frozen, glycerol can be added at the rate of about 1 to 10 volume percent of the concentrate and then the culture is packaged and quick-frozen such as in an isopropanol and dry ice mixture. The stabilized, frozen, concentrated culture is stored at or below minus 20°F(−28.9°C). Held and shipped for use at or below this temperature the product shows no decrease in viability for at least twelve months. The resultant frozen concentrates are preferably standardized at $40$–$60 \times 10^9$–$10^{11}$ cells per milliliter.

The procedure for using the NRRL B-5628 for prophylaxis and therapy of colibacillosis in swine is described in detail hereinafter. Lactobacillus lactis NRRL B-5628 frozen concentrate is removed from the freezer and thawed to a liquid having a temperature of less than about 50°F (10°C) in warm water. The thawed concentrate is placed in a refrigerator at a temperature preferably between about 1° and 5°C. It is then metered into the drinking water of the baby pigs at a rate of (1) ounce of concentrate per gallon of water or fermented milk or fed to the pigs directly as a concentrate per Example 1 or as a dilute fermentate as discussed previously. The concentrate is sufficiently stabilized so that at least about 50% of NRRL B-5628 bacteria in the water survive during a 24 hour period.

If a sow which is expected to farrow is also fed NRRL B-5628 by this method, the incidence of scouring and death of newborn pigs is reduced. Piglets can be removed from the sow shortly after birth and can be fed milk containing NRRL B-5628 with the result that the time when piglets can be removed from sow can be hastened with economic savings.

The following are representative examples of the method of use of Lactobacillus lactis NRRL B-5628.

EXAMPLE 1

A litter of nine newborn pigs were divided into five experimental and four control pigs. Four days were allowed for the litter to become stabilized and to insure healthy pigs. The experimental pigs were fed as follows:

4–15 days — 10 ml of concentrate (between about $1 \times 10^{10}$ to $7.5 \times 10^{10}$ cells/ml.);
15–30 days — 15 ml. of concentrate;
4 to 8 weeks — 30 ml. of concentrate; and
2 to 6 months — 50 ml. of concentrate.

The control pigs were not fed the NRRL B-5628 concentrate. The concentrate was fed daily for a total of 94 days. Fecal specimens were plated daily.

The results show a significant decrease in the *E. coli* (coliform) counts in the experimental as compared to the control pigs. The coliform count in feces of control pigs not fed NRRL B-5628 concentrate was about $10^8$ per gram on first day and still about $10^8$ per gram on 54th day of experiment. While the coliform count in feces of experimental pigs fed NRRL B-5628 concentrate was about $10^8$ per gram on first day, about $10^7$ per gram on 27th day (pigs receiving 15 ml. of concentrate at this time) and about $10^6$ per gram on 54th day (pigs receiving 30 ml. of concentrate at this time). On the average there was about 99.9% reduction of coliform counts in the experimental pigs.

Regarding scouring, an experimental group of pigs were fed NRRL b-5628 during and after weaning. The severity of scouring was reduced in experimental pigs as compared to the control pigs.

EXMAPLE 2

This experiment was done in guinea pigs. A virulent culture of *Salmonella typhimurium* was used. The experimental guinea pig was given *Lactobacillus lactis* NRRL B-5628 for four days before feeding the Salmonella culture, the control guinea pig was not given any NRRL B-5628. Both the guinea pigs were given 3.0 ml of an 18-hour culture of *S. typhimurium*. The control guinea pig died within 36 hours and Salmonella could be isolated from the heart blood, spleen, liver, intestine and fecal samples, in almost pure culture. The experimental guinea pig did not die and Salmonella could not be isolated from fecal samples.

As can be seen from the foregoing Examples: (1) NRRL B-5628 has an inhibitory effect in vivo on the persistence of bacteria in the intestines of pigs. (2) Large numbers of viable NRRL B-5628 must be present to prevent or reduce severity of scouring. This requires at least about $3$–$5 \times 10^{11}$ cells of viable NRRL B-5628 per pig per day. Thus stabilized concentrates with cooling are necessary to insure proper daily dosages. (3) By feeding concentrates of viable NRRL B-5628 to baby pigs the incidence and severity of scouring is reduced. Prevention or reduction of severity of scouring at weaning and just after weaning occurs when pigs are fed daily amount of viable NRRL B-5628 organisms at rate of at least $3$ to $5 \times 10^{11}$ cells per day. (4) Feeding of daily amounts of viable NRRL B-5628 concentrates to farrowing sows prevents or reduces severity of scouring of newborn pigs.

It has also been found that: (1) daily feeding of NRRL B-5628 to sows prevents or reduces severity of mastitis-metrites syndrome; (2) piglets can be removed from sow shortly after birth and fed milk containing NRRL B-5628 thus accruing economic benefits to pig farmer and (3) daily feeding of NRRL B-5628 to piglets increases body weight faster.

Equivalent results can be obtained with NRRL B-5628 in other animals. The economic benefits are best achieved in pigs. Also other known lactic acid producing bacteria can be used in combination with NRRL B-5628 so long as they do not prevent population dominance by NRRL B-5628 in the intestine or other part of the digestive system where such dominance is to be achieved.

I claim:

1. The method for changing the digestive system bacteria in animals which comprises:
   orally feeding a live bacterial composition of *Lactobacillus lactis* NRRL B-5628 mixed with a growth medium to said animals in an amount of at least $1 \times 10^{10}$ cells per day per kg body weight of the animal and for a length of time sufficient to substantially reduce the number of such other digestive system bacteria and to achieve population dominance of NRRL B-5628 in the digestive system.

2. The method of claim 1 wherein the NRRL B-5628 is in the form of an unconcentrated fermentate in the growth medium.

3. The method of claim 1 wherein the amount is fed in range of $1 \times 10^{10}$ to $1 \times 10^{11}$ cells per day per kg body weight of the animal in a feed material.

4. The method of claim 1 wherein the animal is a piglet with *E. coli* in the intestine which can produce scours and wherein the amount of NRRL B-5628 fed in range of $1 \times 10^{10}$ to $1 \times 10^{11}$ cells per day per kg body weight.

5. The method of claim 1 wherein the animal is about to bear young.

6. The method of claim 1 wherein the animal is a chicken and the NRRL B-5628 is in the crop.

7. The method of claim 1 wherein the composition is initially in frozen form with a stabilizing agent and is thawed for use with cooling to maintain the viability.

8. The method of claim 7 wherein the bacterial composition is frozen to below about minus 28.9°C and then thawed for oral feeding to a temperature less than about 10°C.

* * * * *